(12) United States Patent
Pepin

(10) Patent No.: US 7,354,430 B2
(45) Date of Patent: *Apr. 8, 2008

(54) CATHETER INCORPORATING A CURABLE POLYMER LAYER TO CONTROL FLEXIBILITY

(75) Inventor: Henry J. Pepin, Loretto, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/211,800

(22) Filed: Aug. 25, 2005

(65) Prior Publication Data

US 2005/0283135 A1    Dec. 22, 2005

Related U.S. Application Data

(63) Continuation of application No. 10/034,697, filed on Dec. 27, 2001, now Pat. No. 6,945,970.

(51) Int. Cl.
*A61M 25/00* (2006.01)
(52) U.S. Cl. .................. 604/525; 604/523; 138/137; 264/1.38
(58) Field of Classification Search ............... 604/523, 604/525–7; 138/137, 134; 385/115; 428/36.9; 264/1.38
See application file for complete search history.

(56) References Cited

U.S. PATENT DOCUMENTS

| 3,416,531 | A | 12/1968 | Edwards |
| 3,485,234 | A | 12/1969 | Stevens |
| 3,612,058 | A | 10/1971 | Ackerman |
| 4,210,478 | A | 7/1980 | Shoney |
| 4,385,635 | A | 5/1983 | Ruiz |
| 4,419,095 | A | 12/1983 | Nebergall et al. |

(Continued)

FOREIGN PATENT DOCUMENTS

EP    0 277 366 A1    8/1988

(Continued)

OTHER PUBLICATIONS

Kolobow et al., "A New Thin-Walled Nonkinking Catheter for Peripheral Vascular Cannulation," *Surgery*, vol. 68, No. 4, Oct. 1970, pp. 625-626.

*Primary Examiner*—Kevin C. Sirmons
*Assistant Examiner*—Andrew Gilbert
(74) *Attorney, Agent, or Firm*—Crompton, Seager & Tufte, LLC

(57) ABSTRACT

The present invention relates generally to catheters for performing medical procedures including percutaneous transluminal coronary angioplasty. More particularly, the present invention relates to guide catheters, diagnostic catheters and balloon catheters with an improved shaft design. In a preferred embodiment, the present invention includes a catheter shaft comprising an elongate support member having an outer surface, the elongate support member preferably defining a lubricious liner; a first layer disposed over the lubricious liner, a second layer disposed over the first layer, a third layer disposed over the second layer, a fourth layer disposed over the third layer, and a fifth layer disposed over the fourth layer. In preferred embodiments, the first and third layers comprise an ultraviolet-curable epoxy which is cured to desired degrees at select axial locations on the shaft to provide desired stiffness.

6 Claims, 3 Drawing Sheets

U.S. PATENT DOCUMENTS

| | | | |
|---|---|---|---|
| 4,516,970 A | 5/1985 | Kaufman et al. | |
| 4,516,972 A | 5/1985 | Samson | |
| 4,531,943 A | 7/1985 | Van Tassel et al. | |
| 4,563,181 A | 1/1986 | Wijayarathna et al. | |
| 4,588,399 A | 5/1986 | Nebergall et al. | |
| 4,636,346 A | 1/1987 | Gold et al. | |
| 4,690,175 A | 9/1987 | Ouchi et al. | |
| 4,705,511 A | 11/1987 | Kocak | |
| 4,735,620 A | 4/1988 | Ruiz | |
| 4,817,613 A * | 4/1989 | Jaraczewski et al. | 600/435 |
| 4,838,879 A | 6/1989 | Tanabe et al. | |
| 4,842,590 A | 6/1989 | Tanabe et al. | |
| 4,863,442 A | 9/1989 | DeMello et al. | |
| 4,898,591 A | 2/1990 | Jang et al. | |
| 4,899,787 A | 2/1990 | Ouchi et al. | |
| 4,981,478 A | 1/1991 | Evard et al. | |
| 5,017,259 A | 5/1991 | Kohsai | |
| 5,057,092 A | 10/1991 | Webster, Jr. | |
| 5,069,674 A | 12/1991 | Fearnot et al. | |
| 5,078,702 A | 1/1992 | Pomeranz | |
| 5,116,317 A | 5/1992 | Carson, Jr. et al. | |
| 5,160,559 A | 11/1992 | Scovil et al. | |
| 5,163,431 A | 11/1992 | Griep | |
| 5,176,660 A | 1/1993 | Truckai | |
| 5,180,376 A | 1/1993 | Fischell | |
| 5,190,520 A | 3/1993 | Fenton, Jr. et al. | |
| 5,217,440 A | 6/1993 | Frassica | |
| 5,221,270 A | 6/1993 | Parker | |
| 5,221,372 A | 6/1993 | Olson | |
| 5,222,949 A | 6/1993 | Kaldany | |
| 5,234,416 A | 8/1993 | Macaulay et al. | |
| 5,254,107 A | 10/1993 | Soltesz | |
| 5,279,596 A | 1/1994 | Castaneda et al. | |
| 5,306,252 A | 4/1994 | Yutori et al. | |
| 5,308,342 A | 5/1994 | Sepetka et al. | |
| 5,335,305 A | 8/1994 | Kosa et al. | |
| 5,358,493 A | 10/1994 | Schweich, Jr. et al. | |
| 5,423,773 A | 6/1995 | Jimenez | |
| 5,423,774 A | 6/1995 | Fischell et al. | |
| 5,433,200 A | 7/1995 | Fleischhacker, Jr. | |
| 5,445,624 A | 8/1995 | Jimenez | |
| 5,509,910 A | 4/1996 | Lunn | |
| 5,514,108 A | 5/1996 | Stevens | |
| 5,545,151 A | 8/1996 | O'Connor et al. | |
| 5,569,218 A | 10/1996 | Berg | |
| 5,599,319 A | 2/1997 | Stevens | |
| 5,603,705 A | 2/1997 | Berg | |
| 5,658,263 A | 8/1997 | Dang et al. | |
| 5,662,622 A | 9/1997 | Gore et al. | |
| 5,674,208 A | 10/1997 | Berg et al. | |
| 5,676,659 A | 10/1997 | McGurk | |
| 5,711,909 A | 1/1998 | Gore et al. | |
| 5,769,796 A | 6/1998 | Palermo et al. | |
| 5,792,401 A | 8/1998 | Burnham | |
| 5,810,867 A | 9/1998 | Zarbatany et al. | |
| 5,810,874 A | 9/1998 | Lefebvre | |
| 5,836,925 A | 11/1998 | Soltesz | |
| 5,897,537 A | 4/1999 | Berg et al. | |
| 5,906,605 A * | 5/1999 | Coxum | 604/525 |
| 5,911,715 A | 6/1999 | Berg et al. | |
| 5,951,495 A * | 9/1999 | Berg et al. | 600/585 |
| 5,954,651 A | 9/1999 | Berg et al. | |
| 6,017,335 A | 1/2000 | Burnham | |
| 6,030,405 A | 2/2000 | Zarbatany et al. | |
| 6,212,422 B1 | 4/2001 | Berg et al. | |
| 6,240,231 B1 | 5/2001 | Ferrera et al. | |
| 6,258,195 B1 | 7/2001 | Holman et al. | |
| 6,562,021 B1 * | 5/2003 | Derbin et al. | 604/523 |
| 6,945,970 B2 * | 9/2005 | Pepin | 604/525 |
| 2007/0225680 A1 * | 9/2007 | Biggins | 604/526 |

FOREIGN PATENT DOCUMENTS

| | | |
|---|---|---|
| EP | 0 382 974 A1 | 8/1990 |
| EP | 0 473 045 A1 | 3/1992 |
| EP | 0 180 348 B1 | 5/1992 |
| EP | 0 555 088 A2 | 8/1993 |
| EP | 0 555 088 A3 | 8/1993 |
| JP | 4-40652 | 4/1992 |
| JP | 5-84303 | 4/1993 |
| WO | WO 92/15356 | 9/1992 |
| WO | WO 93/15785 | 8/1993 |
| WO | WO 95/29722 | 11/1995 |
| WO | WO 96/20750 | 7/1996 |
| WO | WO 97/14466 | 4/1997 |
| WO | WO 00/03756 | 1/2000 |

* cited by examiner

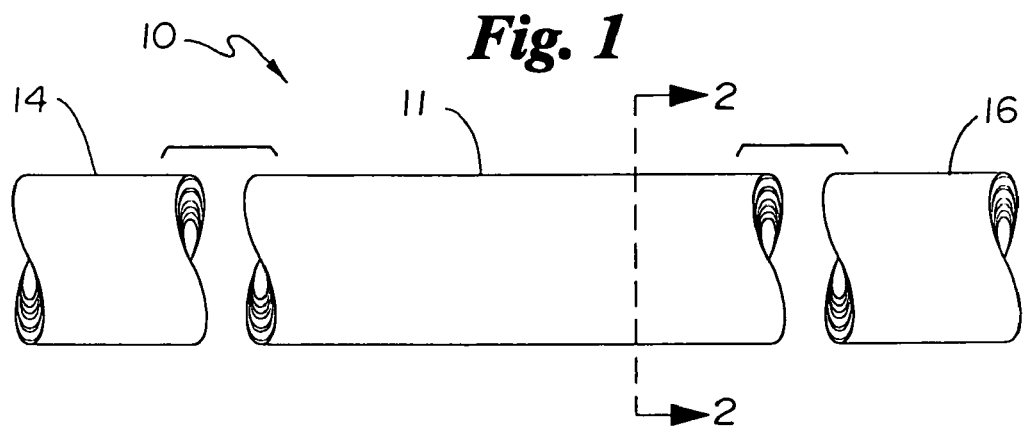
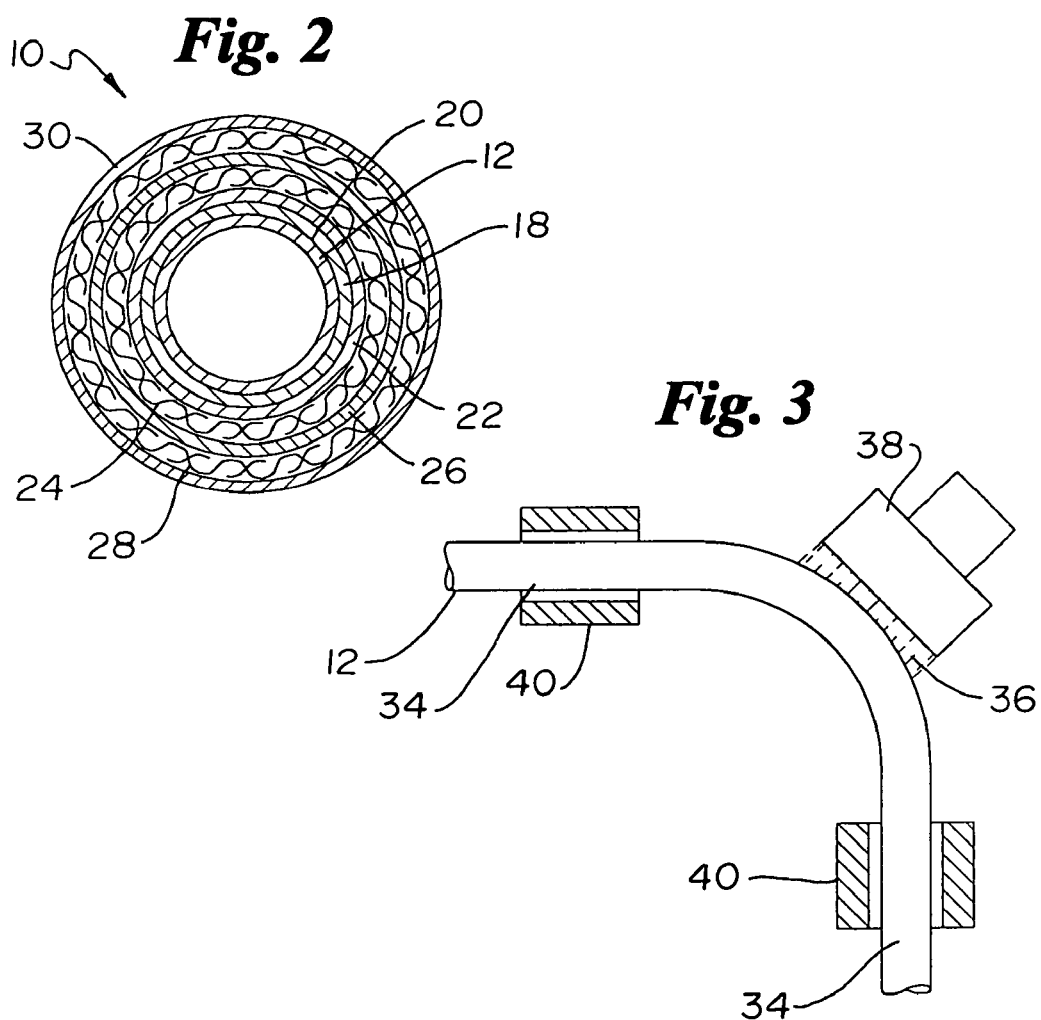

CATHETER INCORPORATING A CURABLE POLYMER LAYER TO CONTROL FLEXIBILITY

CROSS REFERENCE TO PRIOR APPLICATION

This application is a continuation of U.S. application Ser. No. 10/034,697, now U.S. Pat. No. 6,945,970, filed Dec. 27, 2001, the entire disclosure of which is incorporated herein by reference" has been inserted.

FIELD OF THE INVENTION

The present invention relates generally to catheters for performing medical procedures including intravascular diagnosis and treatment. More particularly, the present invention relates to catheters with an improved shaft design.

BACKGROUND OF THE INVENTION

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic procedures utilizing intravascular catheters include percutaneous transluminal angioplasty (PTA) and percutaneous transluminal coronary angioplasty (PTCA). Catheters can also be used in other body lumens or organs for treatment and diagnosis, including the fields of neurology, urology and gastroenterology.

Intravascular catheters and other common catheters are often used in conjunction with a guidewire. A guidewire may be advanced through the patient's vasculature until it has reached a target location. Once in place, a catheter may be threaded onto the guidewire and urged distally until the distal end of the catheter reaches a target location.

One type of common catheter is a guide catheter which can be utilized during coronary angioplasty procedures to aid in delivering a balloon catheter or other interventional medical device to a treatment site in a vessel or other lumen within the body. In one application, a routine coronary angioplasty procedure, a guiding catheter is introduced into a peripheral artery and advanced over a guidewire through the aorta until the distal end of the guide catheter is engaged within the appropriate coronary ostium. Next, a balloon dilatation catheter is introduced over the guidewire and through the guide catheter. In order to function efficiently, guide catheters generally have a relatively stiff main body portion and a relatively flexible distal portion, including a soft distal tip. The stiff main body portion gives the guide catheter sufficient pushability and torqueability to allow the guide catheter to be inserted percutaneously into a peripheral artery or other lumen and advanced adjacent a desired site. However, a distal portion of the guide catheter requires sufficient flexibility so it can track over a guidewire and be maneuvered through a tortuous path to the treatment site.

A second type of common catheter is an angiographic or diagnostic catheter which can be used in evaluating the progress of disease, such as coronary artery disease. Angiography procedures are used to view the patency of selected blood vessels. In carrying out this procedure, a diagnostic catheter is advanced over a guidewire through the vascular system of the patient until the distal end of the catheter is steered into the desired body lumen site. As with the guide catheter, variation in stiffness over the length of the catheter is desired to aid in achieving access to a desired site through the tortuous anatomy.

Another common type of catheter is a balloon dilatation catheter which is adapted for use with a guidewire and typically classified as over-the-wire (OTW) or single operator exchange (SOE) in design. An OTW catheter includes a guidewire lumen extending from the distal tip of the catheter to the proximal end of the catheter. SOE catheters were developed in response to difficulties encountered when exchanging OTW catheters. Accordingly, SOE catheters have a relatively short guidewire lumen relative to the length of the catheter. Therefore, the length of guidewire extending beyond the body of the patient need only be slightly longer than the guidewire lumen of the catheter.

When in use, intravascular or other catheters enter a patient's vasculature or other body lumen at a convenient location and then are urged to a target region. Once the distal portion of the catheter has entered the patient's vascular or other system, the physician may urge the distal tip forward by applying longitudinal forces to the proximal portion of the catheter.

Frequently the path taken by a catheter through the vascular or other system is tortuous, requiring the catheter to change direction frequently. In some cases, it may even be necessary for the catheter to double back on itself. In order for the catheter to conform to a patient's tortuous vascular system, it is desirable that intravascular catheters be flexible, particularly near the distal end.

Further, while advancing the catheter through the tortuous path of the patient's vasculature or other system, physicians often apply torsional forces to the proximal portion of the catheter to aid in steering the catheter. Torsional forces applied at the proximal end must translate to the distal end to aid in steering. It is, therefore, desirable that the proximal portion of an intravascular catheter have a relatively high level of torqueability to facilitate steering.

The need for this combination of performance features suggests that it would be desirable for a catheter shaft to have variable flexibility along the length of the catheter. More specifically, it would be desirable for a catheter to have increased flexibility near the distal end of the catheter shaft and greater stiffness near the proximal end.

One approach used to balance the need for pushability and torqueability while maintaining adequate flexibility has been to manufacture a catheter that has two or more discrete tubular portions over its length, each having different performance characteristics. For example, a relatively flexible distal section may be connected to a relatively rigid proximal section. When a catheter is formed from two or more discrete tubular members, it is often necessary to form a bond between the distal end of one tubular member and the proximal end of another tubular member. This method requires substantial manufacturing steps to assemble the various sections and makes it difficult to manufacture the entire shaft utilizing coextrusion technology. Further, the shaft design is limited by the predetermined flexibility characteristics of each section and can include relatively abrupt changes in flexibility at material changes. A need, therefore, exists for catheter shafts that can be easily manufactured, such as by coextrusion, and yet are capable of having a variable stiffness without assembling components of the shaft.

SUMMARY OF THE INVENTION

The present invention relates generally to catheters for performing medical procedures including percutaneous transluminal coronary angioplasty. More particularly, the present invention relates to catheters with improved shaft designs.

In a preferred embodiment, a catheter shaft comprises an elongate inner member having a proximal end and a distal end. The elongate inner member is generally tubular and defines an outer surface thereon and at least one lumen extending therethrough. Preferably, the elongate member comprises a lubricious material.

In a preferred embodiment, a first layer is disposed over at least a portion of the length of the outer surface of the elongate inner member. Preferably, the first layer comprises a first epoxy layer. The first layer preferably comprises an ultraviolet-curable epoxy or other selectively curable material.

According to a preferred embodiment, a second layer is disposed over at least a portion of the first layer. The second layer preferably comprises a first wire ribbon which is wound in a helical manner in a first direction around at least a portion of the first layer.

In a preferred embodiment, a third layer is disposed over at least a portion of the second layer. Preferably, the third layer comprises a second epoxy layer. The third layer preferably comprises an ultraviolet-curable epoxy or other selectively curable material.

According to a preferred embodiment, a fourth layer is disposed over at least a portion of the third layer. The fourth layer preferably comprises a second wire ribbon which is wound in a helical manner in a second direction, opposite the first direction, around at least a portion of the third layer.

In a preferred embodiment, a fifth layer is disposed over at least a portion of the fourth layer. In an exemplary embodiment, the fifth layer comprises a resin or polymeric material.

According to a preferred embodiment, the catheter shaft can be manufactured by a number of methods including, but not limited to, casting, die casting, molding, extrusion, wire winding, etc. Preferably, the first layer is disposed on the inner member by extrusion. In a preferred embodiment, the second layer may be disposed over the first layer by wire winding methods known by those of ordinary skill in the art. In an exemplary embodiment, the third layer is disposed over the second layer by extrusion. Preferably, the fourth layer may be disposed over the third layer by wire winding methods. In a preferred embodiment, the fifth layer is disposed on the fourth layer by extrusion.

In an exemplary embodiment, at least one layer comprises ultraviolet-curable epoxy. Preferably, two layers comprise ultraviolet-curable epoxy. For example, the first layer and the third layer comprise ultraviolet-curable epoxy. According to alternative embodiments, combinations of the first, second, third, fourth, and fifth layers may comprise ultraviolet-curable epoxy.

In a preferred embodiment, the catheter shaft further comprises a selectively curable region adjacent to at least one flanking region. In a preferred embodiment, at least a portion of the curable region can be irradiated with ultraviolet light from an ultraviolet light source to selectively cure that portion which is irradiated. Preferably, the flanking regions can be shielded from at least a portion of the ultraviolet light by at least one ultraviolet shield. According to a preferred embodiment, exposure to ultraviolet light emitted from an ultraviolet source cures the curable region. Curing the curable region alters the stiffness of the catheter shaft.

In an exemplary embodiment, curing of the first layer or the third layer may take place before, during, or after completion of the manufacturing of the catheter shaft. For example, curing of the first layer may take place before the third layer is disposed on the second layer. Alternatively, the first layer and the third layer may be cured after the catheter shaft is manufactured to completion.

In one preferred embodiment, the catheter shaft may comprise multiple curable regions over the length of the shaft. According to this embodiment of the invention, ultraviolet curing of multiple curing regions may occur sequentially. For example, a first curable region may be cured followed by the curing of a second curable region. Alternatively, multiple curing regions may be cured simultaneously by exposing either a larger portion of the catheter shaft to ultraviolet light or by providing multiple ultraviolet light sources along the length of the catheter shaft.

In a preferred embodiment, the stiffness of the catheter shaft is dependent upon the amount of time a curable region is irradiated with ultraviolet light. For example, irradiating a curable region and an alternate curable region for differing times will result in greater stiffness proximate the region that is irradiated longer. According to this embodiment, the catheter shaft can be constructed to have a selectively variable stiffness over its length without building the shaft from different materials over its length.

According to a preferred embodiment, the stiffness may be varied along the length of the catheter shaft. Preferably, the stiffness may be varied by the amount of curing done along the length of the catheter shaft. For example, it may be desirable for a catheter shaft to have increased stiffness near the proximal end and less stiffness (more flexibility) near the distal end.

BRIEF DESCRIPTION OF THE DRAWINGS

FIG. 1 is a plan view of a portion of a catheter shaft according to a preferred embodiment;

FIG. 2 is a cross-sectional view of the portion of the catheter shaft at 2-2 of FIG. 1;

FIG. 3 is a diagrammatic view of an apparatus for ultraviolet curing a portion of the catheter shaft according to a preferred embodiment of the present invention;

DETAILED DESCRIPTION OF THE PREFERRED EMBODIMENTS

Figure 4:
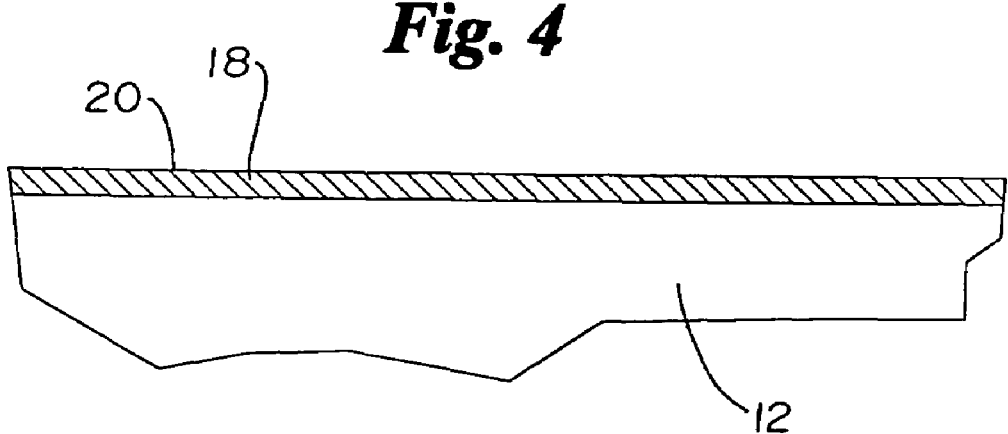
FIG. 4 is a partial plan view of an inner member defining an outer surface thereon.

Referring now to the drawings wherein like reference numerals indicate like elements throughout the several views, FIG. 1 is a partial plan view of a portion of a catheter shaft incorporated into a polymer braid catheter according to a preferred embodiment. According to a preferred embodiment, a catheter shaft 10 comprises at least one elongate generally tubular member 11 having a proximal end 14 and a distal end 16 with at least one lumen therethrough.

In a preferred embodiment, catheter shaft 10 may comprise one or more components of different catheter types. These catheter types include, but are not limited to, a single-operator-exchange catheter, an over-the-wire catheter, a guide catheter, a diagnostic catheter, a balloon catheter, an angioplasty catheter, an atherectomy catheter, etc. A person of ordinary skill in the art would be familiar with different types of catheters appropriate for embodiments of the present invention. The need for and use of a catheter shaft of the present invention in any catheter shaft becomes apparent from the specific catheter disclosed.

According to a preferred embodiment, elongate member 11 can be manufactured from a combination of a number of materials including, but not limited to, stainless steel, metal, nickel alloy, nickel-titanium alloy, hollow cylindrical stock, thermoplastics, high performance engineering resins, polymer, fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyoxymethylene (POM), polybutylene terephthalate (PBT) or polyether block ester. Preferably, elongate support member 11 is manufactured so as to maintain the desired level of flexibility and torqueability according to multiple embodiments of the current invention and includes multiple layers over at least portions of its length which provide selected flexibility.

FIG. 2 is a cross-sectional view of the shaft section of a polymer braid catheter of FIG. 1 according to a preferred embodiment. According to a preferred embodiment, catheter shaft 10 comprises elongate member 11. In a preferred embodiment, elongate member 12 further comprises an inner member 12 defining an outer surface 20. Preferably, inner member 12 can include multiple layers with layer 18 defining a lubricious liner. Alternatively, inner member 12 can be a single layer, preferably a lubricious material. In an exemplary embodiment, lubricious liner 18 may comprise a number of materials known in the art. For example, lubricous liner 18 may comprise polytetrafluoroethylene (PTFE).

In a preferred embodiment, a first layer 22 is disposed over at least a portion of the outer surface 20 of the inner member 12. Preferably, first layer 22 comprises a first epoxy layer. In an exemplary embodiment, first layer 22 comprises a selectively curable material such as an ultraviolet-curable epoxy.

In a preferred embodiment, an epoxy is understood to be one of various thermosetting resins capable of forming tight cross-linked polymer structures. Preferably, epoxies are marked by toughness, strong adhesion, and high corrosion and chemical resistance and are used especially in adhesives and surface coatings. In an exemplary embodiment, an ultraviolet-curable epoxy is understood to be an epoxy that undergoes a physical change, for example, it becomes cured when exposed to ultraviolet light. According to a preferred embodiment of the current invention, curing is understood to be the process of preparing, preserving, or finishing a substance by a chemical or physical means. Preferably, curing alters the physical properties of a substance. In a preferred embodiment, curing ultraviolet-curable epoxy alters the stiffness of catheter shaft 10.

In a preferred embodiment, a second layer 24 is disposed over at least a portion of first layer 22. In an exemplary embodiment, second layer 24 comprises a first wire ribbon. Preferably, the first wire ribbon is wound in a first direction in a helical pattern around first layer 22. Second layer 24 can be manufactured from materials including, but not limited to, stainless steel, metals, nickel alloy, nickel titanium alloy, etc.

In a preferred embodiment, a third layer 26 is disposed over at least a portion of second layer 24. Preferably, third layer 26 comprises a second epoxy layer. In an exemplary embodiment, third layer 26 comprises a selectively curable material such as an ultraviolet-curable epoxy.

In a preferred embodiment, a fourth layer 28 is disposed over at least a portion of third layer 26. In an exemplary embodiment, fourth layer 28 comprises a second wire ribbon. Preferably, the second wire ribbon is wound in a second direction, opposite the first direction in a helical pattern around third layer 26. In a preferred embodiment, fourth layer 28 can be manufactured from materials including, but not limited to, stainless steel, metals, nickel alloy, nickel titanium alloy, etc.

In a preferred embodiment, a fifth layer 30 is disposed over at least a portion of fourth layer 28. In an exemplary embodiment, fifth layer 30 comprises a resin or polymer.

Although the above-disclosed order of layers is preferred, it is recognized that the order can be varied or certain layers omitted. However, at least one layer comprises a selectively curable material such as an ultraviolet-curable epoxy. Preferably, two layers comprise a selectively curable material such as an ultraviolet-curable epoxy. For example, first layer 22 and third layer 26 comprise ultraviolet-curable epoxy. According to alternative embodiments, combinations of first layer 22, second layer 24, third layer 26, fourth layer 28, and fifth layer 30 may comprise ultraviolet-curable epoxy.

FIG. 3 is a diagrammatic view of an apparatus for ultraviolet curing of a shaft member of a polymer braid catheter according to a preferred embodiment. In a preferred embodiment, catheter shaft 10 further comprises a curable region 32 adjacent to at least one flanking or adjacent region 34 which also may be another curable region. Preferably, curable region 32 may comprise any portion of catheter shaft 10. For example, curable region 32 may be near proximal end 14 or distal end 16.

In a preferred embodiment, curable region 32 is irradiated with ultraviolet light 36 emitted from an ultraviolet source 38. Preferably, flanking regions 34 can be shielded from ultraviolet light 36 by at least one ultraviolet shield 40. According to a preferred embodiment, exposure to ultraviolet light emitted from ultraviolet source 38 at least partially cures curable region 32. Preferably, curing curable region 32 stiffens catheter shaft 10.

In an exemplary embodiment, curing of first layer 22 or third layer 26 may take place before, during, or after the manufacturing of catheter shaft 10. For example, curing of first layer 22 may take place before third layer 26 is disposed on second layer 24. Alternatively, first layer 22 and third layer 26 may be cured after catheter shaft 10 is completely manufactured. A person of ordinary skill in the art would be familiar with the appropriate order of manufacturing and curing catheter shaft 10 according to multiple embodiments of the present invention.

In a preferred embodiment, catheter shaft 10 may comprise multiple curable regions. According to this embodiment of the invention, ultraviolet curing of multiple curing regions may occur sequentially. For example, a first curable region may be cured, followed by the curing of a second curable region. Alternatively, multiple curing regions may be cured simultaneously either by exposure to a larger portion of catheter shaft 10 to ultraviolet light or by providing multiple ultraviolet light sources along the length of catheter shaft 10.

According to a preferred embodiment of the current invention, curing is understood to be the process of preparing, preserving, or finishing a substance by a chemical or physical means. Preferably, curing curable region 32 alters the stiffness of catheter shaft 10. In an exemplary embodiment, curing curable region 32 increases the stiffness of catheter shaft 10.

In a preferred embodiment, the stiffness of catheter shaft 10 is dependent upon the amount of time curable region 32 is irradiated with ultraviolet light. For example, irradiating curable region 32 and an alternate curable region will result in greater stiffness within and proximate the region that is irradiated longer.

In an exemplary embodiment, altering the stiffness of catheter shaft 10 may enhance the ability of catheter shaft 10 to transmit torque. For example, increasing the stiffness of catheter shaft 10 near proximal end 14 may enhance torqueability. According to this embodiment, rotation of catheter shaft 10 at one end, for example proximal end 14, will result in a substantially equivalent rotation at another end, for example distal end 16.

According to a preferred embodiment, stiffness may be varied along the length of catheter shaft 10. Preferably, the stiffness may be varied by the amount of curing performed along the length of catheter shaft 10. For example, it may be desirable for a catheter shaft to have increased stiffness near the proximal end and less stiffness (more flexibility) near the distal end. According to this embodiment, catheter shaft 10 may be constructed to comprise a multiplicity of varying amounts of stiffness. Preferably, the stiffness may be altered at any position along the length of catheter shaft 10 by including at least one selectively curable layer over substantially the entire length of the shaft.

FIGS. 4-9 depict a preferred manufacturing method for constructing a catheter shaft according to a preferred embodiment of the invention. According to a preferred embodiment, catheter shaft 10 can be manufactured by a number of methods and combinations of methods including, but not limited to, casting, die-casting, molding, extrusion, wire winding, etc.

FIG. 4 is a partial plan view of an inner member 12 defining an outer surface thereon. Preferably, the inner member 12 is lubricious liner 18, but may include multiple layers. In an exemplary embodiment, inner member 12 may comprise a number of lubricious materials known in the art. For example, inner member 12 may comprise polytetrafluoroethylene (PTFE).

Figure 5:
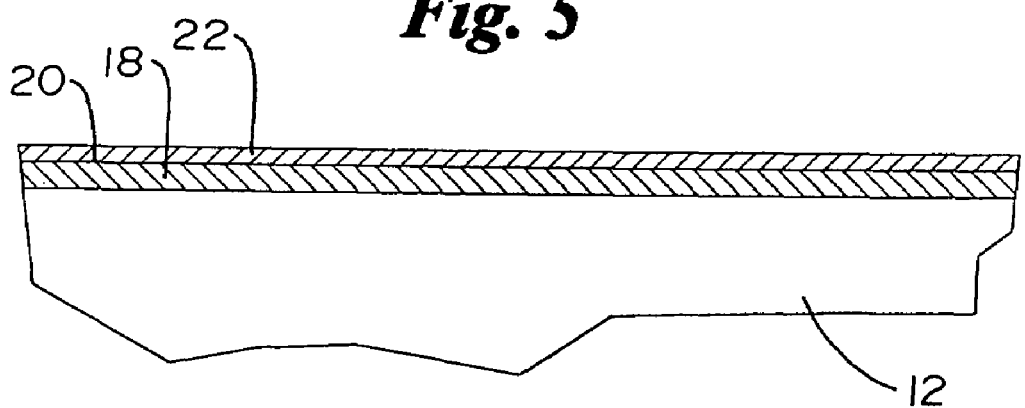
FIG. 5 is a partial plan view of a first layer disposed over at least a portion of the inner member.

FIG. 5 is a partial plan view of a first layer disposed over at least a portion of the inner member 12 of FIG. 4. Preferably, first layer 22 is disposed over the outer surface 20 of inner member 12 by extrusion. According to a preferred embodiment, first layer 22 comprises a selectively curable material such as an ultraviolet-curable epoxy. In an exemplary embodiment, first layer 22 may be cured prior to second layer 24 becoming disposed at first layer 22 or later in the manufacturing process.

Figure 6:
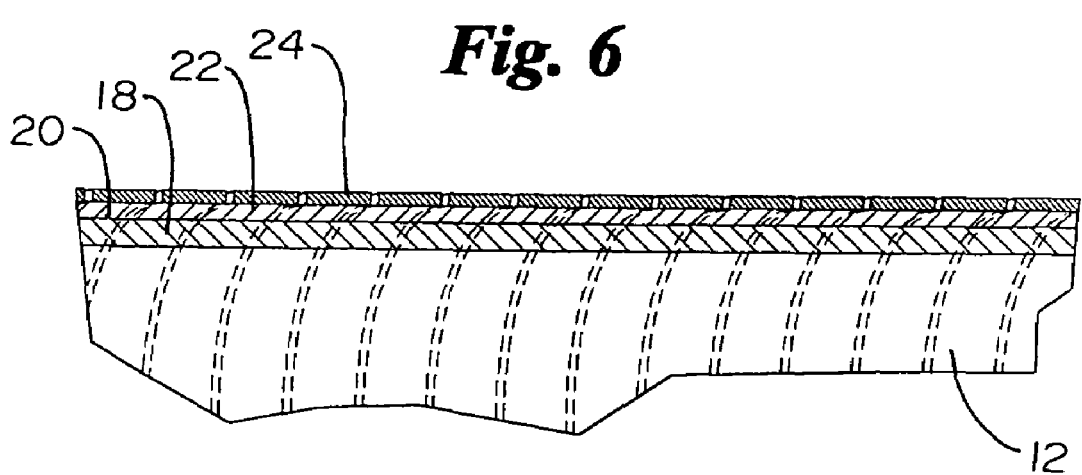
FIG. 6 is a partial plan view of a second layer disposed over at least a portion of the first layer.

FIG. 6 is a partial plan view of a second layer 24 disposed over the first layer 22 of a catheter shaft. In a preferred embodiment, second layer 24 comprises a first wire ribbon. Preferably, second layer 24 may be disposed over first layer 22 by wire winding methods. Wire winding methods are known by a person of ordinary skill in the art according to multiple embodiments of the invention.

Figure 7:
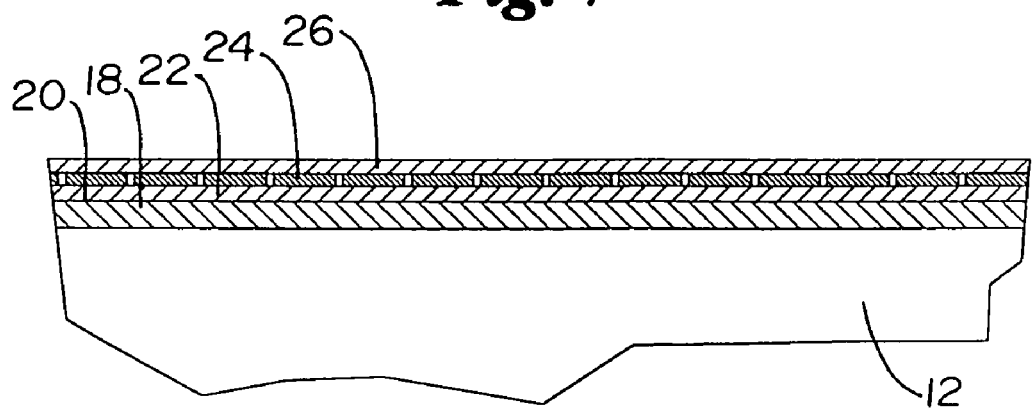
FIG. 7 is a partial plan view of a third layer disposed over at least a portion of the second layer.

FIG. 7 is a partial plan view of a third layer 26 disposed over at least a portion of the second layer 24 of a catheter. In a preferred embodiment, third layer 26 is disposed over second layer 24 by extrusion. According to a preferred embodiment, third layer 26 comprises a selectively curable material such as an ultraviolet-curable epoxy. In an exemplary embodiment, third layer 26 may be cured prior to fourth layer 28 (see FIG. 8) becoming disposed at third layer 26 or later in the manufacturing process.

Figure 8:
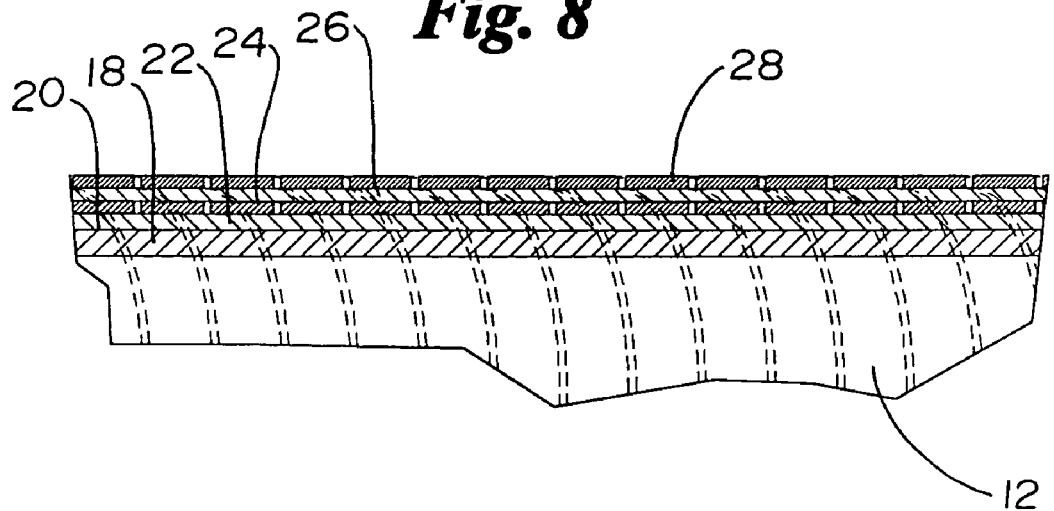
FIG. 8 is a partial plan view of a fourth layer disposed over at least a portion of the third layer.

FIG. 8 is a partial plan view of a fourth layer 28 disposed over at least a portion of the third layer 26 of a catheter. In a preferred embodiment, fourth layer 28 comprises a second wire ribbon. Preferably, fourth layer 28 may be disposed over third layer 26 by wire winding methods known by those of ordinary skill in the art.

Figure 9:
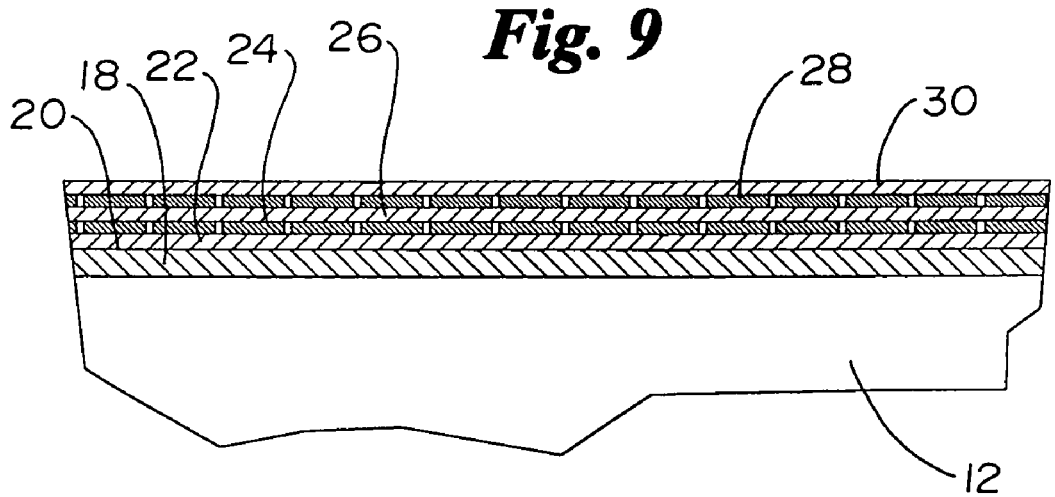
FIG. 9 is a partial plan view of a fifth layer disposed over at least a portion of the fourth layer.

FIG. 9 is a partial plan view of a fifth layer disposed over at least a portion of the fourth layer of a catheter. In a preferred embodiment, fifth layer 30 is disposed over fourth layer 28 by extrusion. According to a preferred embodiment, fifth layer 30 comprises a resin or polymer.

Although a preferred order and number of layers has been described above in the manufacturing step of FIGS. 4-9, it is recognized that the order and number of layers can be altered for alternative embodiments. However, at least one layer comprises a selectively curable material over at least a portion of the length of the shaft which can be selectively cured at desired axial locations to provide desired stiffness in these selected regions.

In use, catheter shaft 10 may be used as part of a catheter to perform an appropriate medical procedure. According to a preferred embodiment, the medical procedure may include, but is not limited to, catheterization, angioplasty, atherectomy, stenosis, restenosis, etc. When performing the medical procedure, catheter shaft 10 may be inserted into the vasculature of a patient and guided to a target region. In a preferred embodiment, curing will impart a desired amount of flexibility in catheter shaft 10. Preferably, the desired flexibility will aid in steering of catheter shaft 10 to a target region.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A support member for use in a catheter shaft, comprising:
    an inner member having an outer surface;
    a first layer comprising ultraviolet-curable epoxy disposed over at least a portion of the outer surface of the inner member, wherein at least a first portion of the first layer has been irradiated with ultraviolet light to alter the stiffness of the support member and wherein a second portion of the first layer has been irradiated to a lesser degree;
    a second layer disposed over at least a portion of the first layer;
    a third layer comprising ultraviolet-curable epoxy disposed over at least a portion of the second layer, wherein at least a portion of the third layer has been irradiated with ultraviolet light to alter the stiffness of the support member;
    a fourth layer disposed over at least a portion of the third layer; and a fifth layer disposed over at least a portion of the fourth layer.

2. The catheter shaft in accordance with claim 1, wherein the second layer comprises a first wire ribbon.

3. The catheter shaft in accordance with claim 2, wherein the first wire ribbon is wound in a helical pattern in a first direction.

4. The catheter shaft in accordance with claim 3, wherein the fourth layer comprises a second wire ribbon.

5. The catheter shaft in accordance with claim 4, wherein the second wire ribbon is wound in a helical pattern in a second direction opposite the first direction.

6. The catheter shaft in accordance with claim 1, wherein the fifth layer comprises a polymer.

* * * * *